(12) United States Patent
Hebert et al.

(10) Patent No.: US 7,491,299 B2
(45) Date of Patent: Feb. 17, 2009

(54) SEMI-CONTINUOUS PHOTOCHEMICAL METHOD AND DEVICE THEREFOR

(75) Inventors: Mélanie Hebert, Jurancon (FR); Jean Ollivier, Arudy (FR); Georges Fremy, Sauveterre de Bearn (FR)

(73) Assignee: Arkema France, Colombes (FR)

( * ) Notice: Subject to any disclaimer, the term of this patent is extended or adjusted under 35 U.S.C. 154(b) by 890 days.

(21) Appl. No.: 10/473,993

(22) PCT Filed: Apr. 4, 2002

(86) PCT No.: PCT/FR02/01175

§ 371 (c)(1),
(2), (4) Date: May 4, 2004

(87) PCT Pub. No.: WO02/081080

PCT Pub. Date: Oct. 17, 2002

(65) Prior Publication Data

US 2005/0040028 A1    Feb. 24, 2005

(30) Foreign Application Priority Data

Apr. 5, 2001    (FR) .................................. 01 04631

(51) Int. Cl.
*C07C 1/00* (2006.01)
*C07F 1/00* (2006.01)
*C07B 45/00* (2006.01)

(52) U.S. Cl. .............................. 204/157.15; 204/157.6; 204/157.76

(58) Field of Classification Search ............ 204/157.15, 204/157.6, 157.76
See application file for complete search history.

(56) References Cited

U.S. PATENT DOCUMENTS

| | | | |
|---|---|---|---|
| 4,140,604 A | 2/1979 | Dimmig | 204/158 R |
| 4,443,310 A | 4/1984 | Arretz et al. | 204/158 R |
| 5,037,618 A | 8/1991 | Hager | 422/186.03 |
| 5,227,140 A | 7/1993 | Hager et al. | 422/186.3 |
| 6,180,805 B1 | 1/2001 | Jansen | 522/653 |
| 6,398,922 B2 * | 6/2002 | Desire | 204/157.94 |
| 2001/0019015 A1 | 9/2001 | Desire | 204/157.94 |
| 2004/0016633 A1 * | 1/2004 | Braun et al. | 204/157.94 |

* cited by examiner

*Primary Examiner*—Edna Wong
(74) *Attorney, Agent, or Firm*—Steven D. Boyd

(57) ABSTRACT

In the photochemical synthetic process in semi-continuous mode according to the invention, a reactor comprising two zones is used, the radiating portion of the lamp(s) being totally immersed in a first zone which is completely filled with reaction medium and spills off via an overflow into a second zone whose volume is sufficient to contain the volume of reaction medium originating from the first zone and corresponding substantially to the volume of the reagent(s) gradually introduced.

9 Claims, 2 Drawing Sheets

SEMI-CONTINUOUS PHOTOCHEMICAL METHOD AND DEVICE THEREFOR

FIELD OF THE INVENTION

The present invention relates to the field of photochemical processes and its subject is, more particularly, a photochemical process performed semi-continuously, and also a device for carrying it out.

BACKGROUND OF THE INVENTION

The expression "process performed in semi-continuous mode" means here a process in which at least one of the reagents is, from the start of the reaction, introduced in total into the photochemical reactor while at least one of the reagents is introduced gradually into the reactor as it is consumed. Such a procedure is occasionally found to be necessary in order to observe the optimum synthetic conditions.

In a photochemical process operating in liquid medium, it is necessary for the radiating portion of the lamp to be constantly fully immersed in the liquid reaction medium. This total immersion is essential so as not to illuminate a gas phase whose behaviour, under ultraviolet irradiation, may prove to be hazardous or an inconvenience for the reaction under consideration. Thus, for example, in the synthesis of sulphides and mercaptans by photochemical reaction of an alkene with a mercaptan or hydrogen sulphide, UV irradiation of the gas phase may produce elemental sulphur which is a well-known inhibitor of free-radical reactions such as those carried out to produce sulphides or mercaptans. Moreover, total immersion of the radiating portion of the lamp also makes it possible to remove, via the reaction medium, the heat emitted by the lamp; this arrangement simplifies the process and minimizes the equipment required (jacket, cooling-water circuit, exchangers, etc.).

However, this arrangement is incompatible with the use of a semi-continuous process in which the gradual introduction of at least one of the reagents entails an increase in the volume of the reaction medium in a reactor of fixed geometry.

SUMMARY OF THE INVENTION

According to the invention, this problem has been solved by carrying out the photochemical process in a reactor comprising two zones, the radiating portion of the lamp being totally immersed in a first zone which is completely filled with reaction medium and spills off via an overflow into a second zone whose volume is sufficient to contain the volume of reaction medium originating from the first zone and corresponding substantially to the volume of the reagent(s) gradually introduced.

Figure 1:
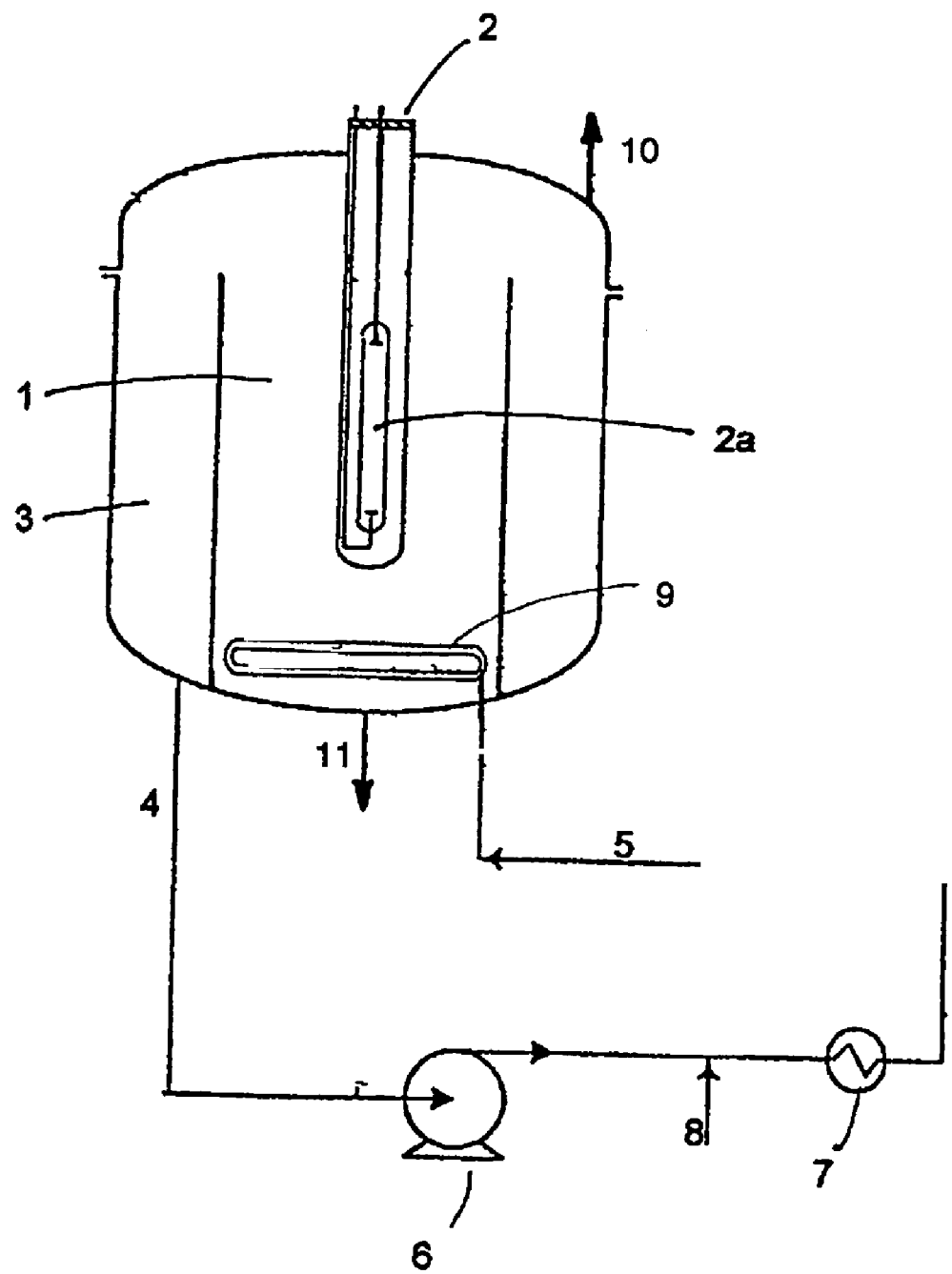
FIG. 1 shows the essential components of a reactor in accordance with the present invention.

The invention will be understood more clearly in the light of the scheme in the attached FIG. 1 which shows essential components of a reactor in accordance with the present invention. This reactor comprises a reaction zone (1) completely filled with reaction medium in which is at least totally immersed the radiating portion (2a) of a UV lamp (2) and, adjacent to the zone (1), a jacket zone (3) into which spills out the overflow from zone (1), pipes (4) and (5) for recycling, via at least one pump (6) and a heat exchanger (7), into the zone (1) via the distributor (9) the reaction medium after the additional reagent(s) has(have) been introduced therein via at least one pipe (8), a gassing vent (10) and a pipe (11) allowing the zone (1) of the reactor to be emptied.

In the preferred embodiment as represented in FIG. 1, the cylindrical zone (1) and the jacket zone (3) are coaxial. However, since the inventive concept is to work in a reactor with two zones, one filled with reaction medium in which is totally immersed the radiating portion of the lamp, and the other collecting the overflow from the first zone, it would not constitute a departure from the context of the present invention to work in a reactor in which the two zones (1) and (3) were not coaxial.

In accordance with the present invention, the lamp (2) is installed in the zone (1) such that at least all of the radiating portion (approximately 65% of the length of the lamp) is immersed in the reaction medium, the top portion (about 35%) corresponding to the electrical portion (supply cable) not needing to be immersed. However, it would not constitute a departure from the context of the present invention to immerse a greater portion of the lamp than that corresponding to the radiating portion.

As mentioned above, the volume of the zone (3) should be sufficient to contain the volume of reaction medium originating from the zone (1) and corresponding substantially to the volume of the reagent(s) gradually introduced. The ratio between the volumes of the zones (1) and (3) thus depends on the reaction under consideration and may be calculated easily by a person skilled in the art from the reaction parameters (volume of zone 1, reaction time, volumes of the reagents, etc.).

The process and the device according to the invention have been designed for the photochemical manufacture of methyl ethyl sulphide ($CH_3SCH_2CH_3$) from ethylene and methyl mercaptan, but they are also useful not only for the photochemical manufacture of other sulphides or mercaptans, but also more generally for any photochemical synthesis requiring the continuous supply of one or more reagents into the reactor during an operation.

The photochemical synthesis of sulphides and mercaptans by reacting an alkene with a mercaptan or hydrogen sulphide, optionally in the presence of a photoinitiator is generally carried out with a light source consisting of at least one low-pressure mercury lamp or any other source which delivers UV radiation of wavelengths between 200 and 400 nm. This reaction is preferably performed at a pressure above atmospheric pressure which may range from 0.1 to 50 bar relative depending on the starting alkene and the starting mercaptan (or $H_2S$); for the synthesis of methyl ethyl sulphide, the process is preferably performed at a pressure of between 2 and 10 bar relative. As regards the reaction temperature, it is generally between −20 and 120° C. (preferably between 10 and 90° C.) and depends not only on the cooling system but also on the chosen working pressure.

For the manufacture of methyl ethyl sulphide, the ratio of the volume V1 of the zone (1) to the volume V3 of the zone (3) is generally between 0.4 and 0.7.

Figure 2:
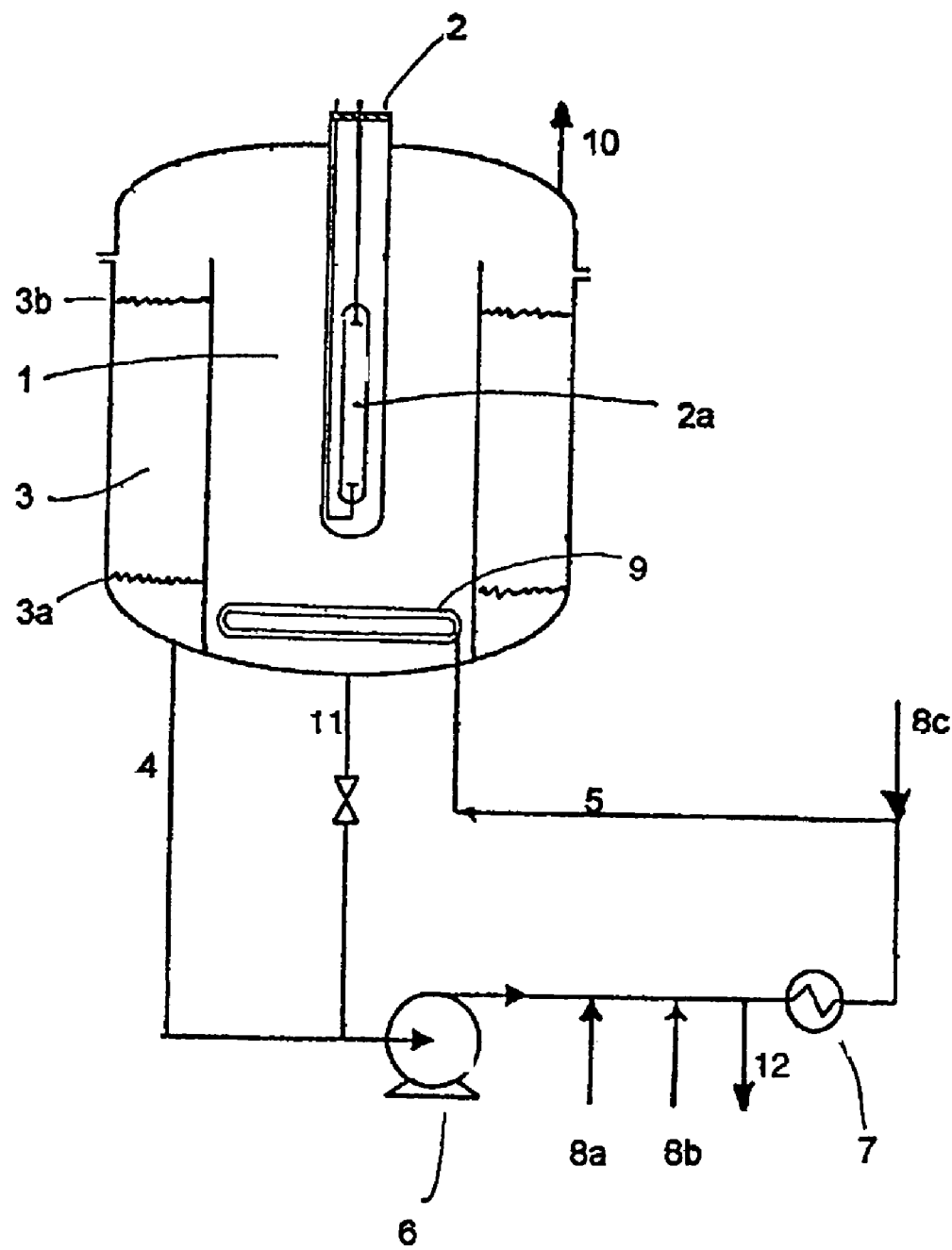
FIG. 2 represents a device which is suitable for the semi-continuous manufacture of sulphides from mercaptan and an alkene in the presence of photoinitiator.

The scheme in the attached FIG. 2 represents a device which is suitable for the semi-continuous manufacture of sulphides from a mercaptan and an alkene in the presence of a photoinitiator. In this scheme, the inlet pipes (8a), (8b) and (8c) respectively, those of the mercaptan, the photoinitiator and the alkene. The operation consists firstly in filling the zone (1) with the mercaptan until it overflows into the annular zone (3) to a level (3a) which is sufficient to be able to start the pump (6) used to circulate and stir the reaction medium. After loading the mercaptan via inlet pipe (8a), the pump (6) is switched on and the liquid originating from the zone (3) is cooled in the exchanger (7) and then conveyed to the zone (1). Once the circulation is stable, the lamp (2) is switched on and, after a few minutes of establishing the working regime, the reaction starts with the simultaneous introduction of the photoinitiator via the inlet pipe (8b), and of the alkene via the inlet pipe (8c). Since the volume of the reaction medium increases gradually with the introduction of the photoinitiator and of the alkene, the level in the zone (3) rises up to, for example, the level (3b), but the radiating portion of the lamp always remains totally immersed in the reaction medium and at the same time cooled thereby. When the desired amount of mercaptan has been reacted, the supply of alkene and photoinitiator are stopped and the lamp is then switched off. After degassing via the vent (10), the reaction medium is collected via the pipe (12) and optionally conveyed to a purification zone which, since it does not form the subject of the invention, is not represented herein.

The example which follows illustrates the invention without limiting it.

EXAMPLE

In the device described in FIG. 2, methyl ethyl sulphide was prepared using, as light source, a low-pressure mercury lamp which re-emits by fluorescence radiation in the region of 350 nm. This 58 watt lamp was placed axially in the zone (1) of the reactor having a total capacity of 50 liters, the volumes V1 and V3 being 15 and 35 liters, respectively.

23.2 kg of liquid methyl mercaptan were initially loaded so as to fill the zone (1) and to overflow into the zone (3). Ethylene was introduced at a flow rate of 1.03 kg/hour and the photoinitiator (2,2-dimethoxy-2-phenylacetophenone as a solution at 200 g/l in methyl ethyl sulphide) was introduced at a flow rate such that the concentration of 2,2-dimethoxy-2-phenylacetophenone in the reaction medium was 0.1 g/liter. The pressure in the reactor rose from 3 to 9 bar absolute; the temperature was maintained at 45° C.

The supply of ethylene and photoinitiator was stopped after 13.1 hours and the reaction was left to continue while keeping the reaction medium in circulation for about one hour.

The amount of crude methyl ethyl sulphide collected after depressurization in the flow 12 was 35.95 kg. At atmospheric pressure and at room temperature, this product had the following weight composition:

| Constituent | % by weight |
|---|---|
| Fractions | 0.29 |
| Methyl mercaptan | 0.001 |
| Ethyl mercaptan | 0.004 |
| Dimethyl sulphide | 0.07 |
| Methyl ethyl sulphide | 99.57 |
| Diethyl sulphide | 0.002 |
| Heavy fractions | 0.06 |

The gaseous effluent, exiting via 10, weighed 0.76 kg and had the following weight composition:

| Constituent | % by weight |
|---|---|
| Fractions | 39.3 |
| Methyl mercaptan | 60.6 |

From these results, the yield of methyl ethyl sulphide is established at 97% relative to the ethylene and at 98% relative to the methyl mercaptan.

The invention claimed is:

1. A semi-continuous photochemical synthesis process comprising:
introducing a first reagent selected from a mercaptan or hydrogen sulphide into a first reaction zone of a photochemical reactor which comprises two zones, in a quantity sufficient to totally immerse a radiating portion of a lamp therein; thereafter
activating said lamp; and thereafter
gradually introducing a second alkene reagent into said first reaction zone, forming a reaction medium comprising said first reagent and said second alkene reagent; said second alkene reagent introduced in sufficient quantity to cause said reaction medium in said first reaction zone to overflow said first reaction zone and spill off, via an overflow, into a second zone of said photochemical reactor whose volume is sufficient to contain said overflow of said reaction medium corresponding substantially to the volume of said second alkene reagent introduced.

2. Process according to claim 1, in which said lamp comprises one or more lamps delivering UV radiation of wavelengths between 200 and 400 nm.

3. Process according to claim 1, wherein said photochemical reactor is maintained at a pressure ranging from 0.1 to 50 bar relative.

4. Process according to claim 3, wherein said photochemical reactor is maintained at a pressure of between 2 and 10 bar relative.

5. Process according to claim 1, wherein said photochemical reactor is maintained at a temperature of between −20 and 120° C.

6. Process according to claim 1, wherein said photochemical reactor is maintained at a temperature of between 10 and 90° C.

7. Process according to claim 1, in which the mercaptan is methyl mercaptan and the second alkene reagent is ethylene.

8. Process according to claim 1, in which the ratio of the volume of the first zone to the volume of the second zone is between 0.4 and 0.7.

9. Process according to claim 1, further comprising gradually introducing a photoinitiator into said first reaction zone.

* * * * *